United States Patent
Bristow et al.

(10) Patent No.: US 10,537,847 B2
(45) Date of Patent: Jan. 21, 2020

(54) METHOD AND APPARATUS FOR TREATING OFFGASES IN A ACETIC ACID PRODUCTION UNIT

(71) Applicant: BP CHEMICALS LIMITED, Middlesex (GB)

(72) Inventors: Timothy Crispin Bristow, East Yorkshire (GB); Paul David Williams, Dyce (GB)

(73) Assignee: BP Chemicals Limited, Middlesex (GB)

( * ) Notice: Subject to any disclaimer, the term of this patent is extended or adjusted under 35 U.S.C. 154(b) by 170 days.

(21) Appl. No.: 15/315,154

(22) PCT Filed: Jun. 16, 2015

(86) PCT No.: PCT/EP2015/063495
§ 371 (c)(1),
(2) Date: Nov. 30, 2016

(87) PCT Pub. No.: WO2015/193328
PCT Pub. Date: Dec. 23, 2015

(65) Prior Publication Data
US 2018/0117526 A1 May 3, 2018

(30) Foreign Application Priority Data

Jun. 17, 2014 (EP) .................................. 14172828

(51) Int. Cl.
*B01D 53/14* (2006.01)
*B01D 53/18* (2006.01)
(Continued)

(52) U.S. Cl.
CPC ..... *B01D 53/1493* (2013.01); *B01D 53/1406* (2013.01); *B01D 53/1487* (2013.01);
(Continued)

(58) Field of Classification Search
CPC ......... C07C 53/08; C07C 51/12; C07C 51/42; C07C 51/48; B01D 2252/2021;
(Continued)

(56) References Cited

U.S. PATENT DOCUMENTS

| 4,241,219 A | 12/1980 | Wan |
| 5,696,284 A | 12/1997 | Baker et al. |

(Continued)

FOREIGN PATENT DOCUMENTS

| CN | 1651388 | 8/2005 |
| CN | 1325459 C | 7/2007 |

(Continued)

*Primary Examiner* — Cabrena Holecek
(74) *Attorney, Agent, or Firm* — McDonnell Boehnen Hulbert & Berghoff LLP

(57) ABSTRACT

A method for scrubbing off-gas generated in production units for the manufacture of acetic acid and an apparatus therefor. The method comprises supplying off-gas and acetic acid solvent at a tick-over flow rate to an acetic acid scrubbing unit, withdrawing off-gas from the scrubbing unit, supplying withdrawn off-gas to a methanol scrubbing unit, scrubbing the off-gas therein with methanol solvent and withdrawing scrubbed off-gas from the methanol scrubbing unit.

17 Claims, 1 Drawing Sheet

(51) Int. Cl.
   *C07C 51/12*      (2006.01)
   *C07C 51/48*      (2006.01)
   *C07C 51/42*      (2006.01)

(52) U.S. Cl.
   CPC .............. B01D 53/18 (2013.01); C07C 51/12 (2013.01); C07C 51/42 (2013.01); *B01D 2252/205* (2013.01); *B01D 2252/2021* (2013.01)

(58) Field of Classification Search
   CPC .......... B01D 2252/205; B01D 53/1406; B01D 53/1487; B01D 53/1493; B01D 53/18
   See application file for complete search history.

(56) References Cited

U.S. PATENT DOCUMENTS

| | | |
|---|---|---|
| 2009/0088587 A1 | 4/2009 | Powell |
| 2009/0270651 A1 | 10/2009 | Zinobile et al. |
| 2011/0190549 A1 | 8/2011 | Horton et al. |
| 2014/0065040 A1 | 3/2014 | Katz et al. |

FOREIGN PATENT DOCUMENTS

| | | | |
|---|---|---|---|
| CN | 100358610 C | 1/2008 | |
| CN | 1289172 C | 12/2008 | |
| JP | S61-58803 A | 3/1986 | |
| WO | 2004080941 A2 | 9/2004 | |
| WO | 2009134332 A2 | 11/2009 | |
| WO | WO 2012/064689 A1 | 5/2012 | |
| WO | WO-2012064689 A1 * | 5/2012 | ......... B01D 53/1418 |

* cited by examiner

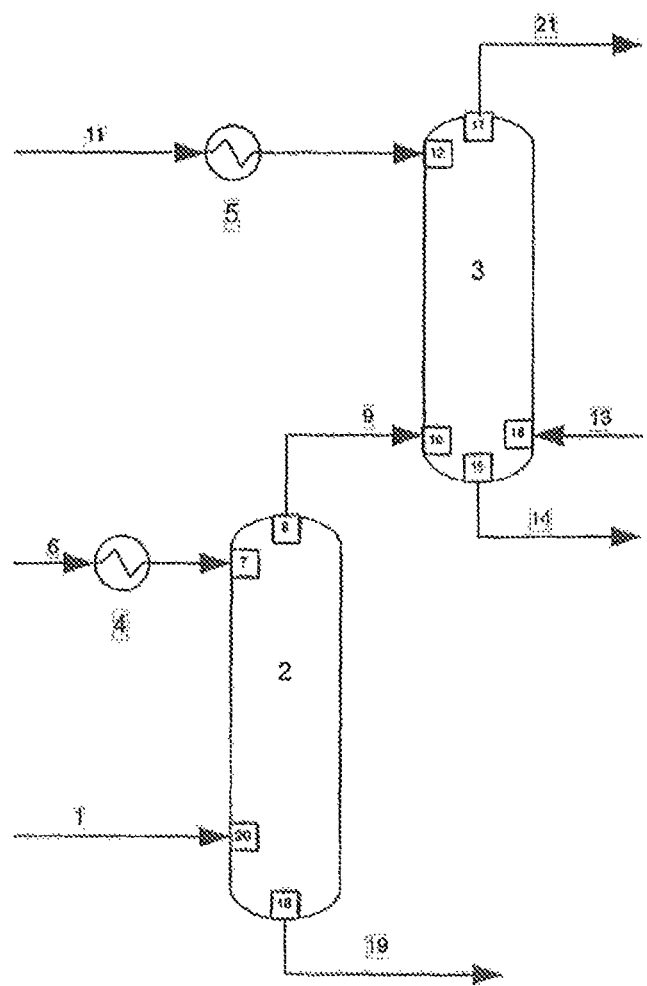

METHOD AND APPARATUS FOR TREATING OFFGASES IN A ACETIC ACID PRODUCTION UNIT

This application is the U.S. national phase of International Application No. PCT/EP2015/063495 filed Jun. 16, 2015 which designated the U.S. and claims priority to European Patent Application No. 14172828.7 filed Jun. 17, 2014, the entire contents of each of which are hereby incorporated by reference.

The present invention relates to a method for scrubbing off-gas generated in production units for the manufacture of acetic acid, such as off-gas generated in production units for the manufacture of acetic acid and/or co-manufacture of acetic acid and acetic anhydride by the carbonylation of methanol in the presence of a Group VIII metal carbonylation catalyst, and an apparatus therefor.

Commercially, acetic acid has been manufactured for many years by carbonylating methanol with carbon monoxide in the presence of a group VIII carbonylation catalyst. Typically, carbon monoxide is contacted with methanol in the presence of a rhodium or an iridium homogeneous or heterogeneous carbonylation catalyst, methyl iodide and water in a reactor. In general, acetic acid product may be recovered by withdrawing crude acetic acid product from the reactor and separating the acetic acid product in one or more flash and/or distillation stages from the other components such as the Group VIII metal carbonylation catalyst, methyl iodide, methyl acetate, and water.

In the process of manufacturing acetic acid and/or co-manufacture of acetic acid and acetic anhydride, off-gas is typically withdrawn at several stages of the process, such as from one or more of the reactor and distillation stages. Off-gas is removed to keep the standing concentration of undesirable gaseous reaction by-products and inert gases to an acceptable level.

High pressure off-gas obtained from the carbonylation reactor has historically been vented from the reactor to maintain the carbon monoxide partial pressures in the reactor within a suitable range to ensure catalyst stability. This venting of the high pressure off-gas from the reactor enables the removal of inert gas components from the reactor, thus maintaining the carbon monoxide partial pressure, but this has the negative impact of removing carbon monoxide from the reactor which is then not available for reaction. The amount of high pressure off-gas bleed required has been reduced to near zero on many plants due to the high solubility and possible entrainment of carbon monoxide and other gases in the reactor solution itself. This high solubility carries the gases down through the flashing line to be further reacted away in a secondary reactor and any excesses may then be vented in a low pressure off-gas system. This allows the high pressure off-gas vent to be closed or substantially closed during normal operating conditions whilst still maintaining adequate carbon monoxide partial pressure above the reaction solution.

When a high pressure off-gas stream is taken from the primary reactor to purge inert components from the reactor and maintain the required carbon monoxide partial pressure in the vapour space, the high pressure off-gas stream has typically been routed to a dedicated high pressure absorption unit using chilled acetic acid to remove methyl iodide prior to the off-gas being sent for disposal. The high pressure off-gas has historically been passed through a condenser and a knockout pot to remove condensable vapour and the condensed liquid has typically been returned into the reaction system. The condenser and knockout pot arrangement has also facilitated the provision of a condensable free sample of the high pressure off-gas which may be analysed in order to indicate the level of inert compounds in the reactor vapour phase and the partial pressure of carbon monoxide in the reactor.

In more recent developments, high pressure off-gas removed from methanol carbonylation reactors has not been sent to an absorption unit but has instead been routed into the flash separation zone of the acetic acid production system, wherein the reaction liquid is flash separated to facilitate return of catalyst to the reactor and to effect a crude first separation of the acetic acid product. Introducing the high pressure off-gas from the reactor thus combines it with the low pressure off-gas generated from the carbon monoxide and other non-condensable gases which are dissolved in the reactor liquid. The combined off-gas may then pass through the distillation section and into a combined and/or a low pressure off-gas scrubbing system via the overhead condensers, prior to disposal. Advantageously, passing high pressure off-gas into the flash separation zone enables several equipment items to be eliminated, such as dedicated high pressure absorption systems and associated refrigeration and pumps. Additionally, by passing high pressure off-gas to the flash separation zone it is not necessary to remove condensable vapour from the high pressure off-gas; a small condenser and knockout pot may still be included to remove condensables prior to the high pressure off-gas being sent to any analysis system.

Further, since the flash separation zone is at a lower pressure than the reactor, it is therefore possible to introduce the high pressure off-gas into the flash separation zone via a control valve to enable control of the high pressure off-gas flow and therefore the concentration of inert gases in the reactor vapour space. In such a scheme there is no necessity to increase the high pressure off-gas pressure through compression.

Alternatively, it may be desirable to introduce high pressure off-gas into the process upstream of the flash separation zone; however, this would require the high pressure off-gas pressure to be increased. This can typically be achieved through compression using turbomachinery and such equipment requires the gas to be compressed to have low amounts of condensable components; therefore, condensation and knockout of condensable vapour would be required in the provision of the off-gas to the compressor to ensure that the off-gas would have low amounts of condensable components.

The exact composition of off-gas will vary depending on the specific carbonylation process conditions employed but typically it will contain carbon monoxide, inert gases and reaction by-product gases, iodide compounds, mainly methyl iodide, and it may also contain low levels of methyl acetate, acetic acid and water.

Off-gas is generally processed by scrubbing it with a stumble scrubbing solvent to recover valuable components, such as methyl iodide, which may be ultimately returned to the reactor. The scrubbed off-gas comprising inert and by-product gases is usually burned. A variety of scrubbing solvents may be employed, for example acetic acid and methanol. In such scrubbing processes, methyl iodide becomes absorbed in the scrubbing solvent and off-gas containing a reduced amount of methyl in iodide is removed from the scrubbing unit, typically as an overhead.

U.S. Pat. No. 4,241,219 describes a process for the recovery of halogen values from an effluent gas stream obtained in the carbonylation of methyl acetate and/or methyl ether by scrubbing the effluent gas stream with at least one of the products of the carbonylation reaction having a boiling point above 100° C. for example acetic acid.

Typically, mixtures of acetic acid scrubbing solvent containing absorbed methyl iodide are separated to recover the acetic acid and methyl iodide components. Separation of these components may be carried out using conventional processes, for example stripping processes. Recovered acetic acid may be returned to the scrubbing system for re-use therein. If desired, recovered methyl iodide may be returned to the reactor. Thus, using acetic acid as a scrubbing solvent suffers from the disadvantage that additional processing equipment is required for its recovery leading to an increase in capital expenditure and operating costs of the acetic acid production process.

The use of methanol as a scrubbing solvent for off-gas generated in acetic acid production processes can provide certain advantages over the use of acetic acid. Typically, methanol is used as a feedstock in the production of acetic acid and used methanol scrubbing solvent from a scrubbing unit may be sent directly to the reactor without the prior recovery of methanol therefrom. As a result, the installation of processing equipment for methanol recovery and associated capital and operating costs can be avoided. Scrubbing processes which employ methanol as a scrubbing solvent are described, for example in CN 100358610C, CN 1289172C, JP 61058803, WO 2004/080941, CN 1325459C and WO 2009/134332.

CN 100358610C describes a method for the recovery of useful components from methyl iodide containing off-gas by absorption with methanol and condensing the vent gas to recover methanol.

CN 1289172C describes a two-stage method for the recovery of useful components from methyl iodide containing off-gas by absorption with methanol in low pressure and high pressure absorption towers.

JP 61058803 describes a method of recovering iodine compounds from waste gas produced during the production of acetic acid by bringing the waste gas into countercurrent contact with methanol.

WO 2004/080941 describes a method of manufacturing acetic acid by way of a heterogeneous catalytic reaction in a bubble column reactor and in which process there may be employed a gas absorption operation using methanol as absorbent liquid to collect useful substances from the off-gas.

CN 1325459C describes a method for recycling the light components of off-gas in the production of acetic acid/acetic anhydride by carbonylation, in which off-gas is subjected to a two-stage absorption process wherein the first absorption solution is one or more of methyl acetate, methanol and acetic acid and the second absorption solution is acetic acid, water or a mixture thereof.

WO 2009/134332 describes a methanol carbonylation system which includes a single absorber tower adapted for receiving a vent gas stream and removing methyl iodide therefrom with a scrubber solvent, the absorber lower being coupled to a first and second scrubber solvent sources which are capable of supplying different first and second scrubber solvents. A switching system includes valves for alternatively providing first or second scrubber solvents to the absorber tower.

Under non-steady state conditions, such as at plant start-up, plant shut-down or plant trips/upsets, it is frequently the case in acetic acid production processes that the supply of methanol to the reactor and/or scrubbing units becomes limited and may be ceased entirely. This is clearly disadvantageous for those acetic acid production processes which use methanol as an off-gas scrubbing solvent. Switching systems, such as those described in WO 2009/134322, provide for the use of different scrubbing solvents in a single scrubbing column. Whilst the use of a single scrubbing column may reduce capital requirements and operating costs, the use of a switching system may entail disadvantages on changeover from one scrubbing solvent to a different scrubbing solvent, such as disadvantages associated with undesirable mixing of scrubbing solvents and complexities associated with multiple scrubbing solvent supply lines.

In general, the efficiency with which off-gas is scrubbed with a solvent is maximised by utilising a scrubbing solvent which has been cooled prior to use. In general, a scrubbing solvent is cooled by passing the solvent through a heat exchange unit configured to reduce the temperature of the solvent prior to its use in a scrubbing unit. The use of multiple scrubbing solvents which have different physical properties, such as different freezing points, in the same scrubbing unit may give rise to certain disadvantages. For example, at atmospheric pressure, acetic acid freezes at about +17° C. whereas methanol freezes at about −98° C. Cooling methanol to temperatures below about +17° C. could, on switching from methanol to acetic acid, give rise to acetic acid freezing within the scrubbing unit which may result in a total loss of scrubbing efficiency and a release of methyl iodide to the atmosphere. In such switching systems, the use of dedicated heat exchangers to cool each of the different scrubbing solvents may not overcome the problem as a scrubbing unit and the packing within the scrubbing unit tend to cool to a temperature close to that of the scrubbing solvent employed.

It is suggested in the art that methanol having been used to scrub off-gas may be removed from the scrubbing unit and transferred to storage/surge tanks used to store fresh methanol. Typically, used methanol streams from scrubbing units contain significant levels of methyl iodide. Transfer of such streams to methanol storage/surge tanks may result in the methanol supply to a scrubbing unit being contaminated with methyl iodide. If a methanol supply is contaminated with a sufficiently high level of methyl iodide, the methyl iodide content of off-gas discharged from a scrubbing unit may be such that it exceeds environmental specification limits for methyl iodide emissions.

In general, methanol feedstock for acetic acid production processes is pumped to the reactor from methanol storage/surge tanks using at least one high pressure pump, typically a set of high pressure pumps. It is suggested in the art that used methanol streams may be transferred from a scrubbing unit into the reactor. However, such an arrangement would appear to rely on the use of an additional high pressure pump or set of high pressure pumps; one pump or set of pumps on the base of a scrubbing unit to pump used methanol streams from the scrubbing unit to the reactor and a second pump or set of pumps on the discharge of a methanol storage/surge tank to pump fresh methanol to the reactor.

As used herein, reference to a "high pressure pump" or "high pressure pumps" are references to pumps with discharge head pressure substantially above atmospheric pressure, typically having a discharge head pressure of at least 20 barg, more typically at least 25 barg. High speed pump(s) may be employed as high pressure pumps(s).

It would thus be desirable to provide an alternative method of scrubbing off-gas streams generated in production processes for the manufacture of acetic acid, and in particular off-gas streams generated in production processes for the manufacture of acetic acid by the carbonylation of methanol, which method avoids or at least mitigates the above-mentioned disadvantages.

Accordingly, the present invention provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises:

(i) supplying off-gas and acetic acid to the acetic acid scrubbing unit and withdrawing off-gas therefrom;

(ii) supplying withdrawn off-gas and methanol to the methanol scrubbing unit and contacting the off-gas and methanol therein to produce scrubbed off-gas; and (iii) withdrawing from the methanol scrubbing unit scrubbed off-gas, wherein the acetic acid is supplied to the acetic acid scrubbing unit at a tick-over flow rate.

By 'tick-over' flow of acetic acid is meant throughout this specification and in the claims, a flow rate of acetic acid to the acetic acid scrubbing unit which is insufficient to reduce or substantially reduce the methyl iodide content of off-gas fed to the scrubbing unit, such that off-gas withdrawn from the acetic acid scrubbing unit has not been scrubbed and retains all or substantially all of its methyl iodide content. Consequently, under steady-state conditions, off-gas withdraw from the acetic acid unit requires scrubbing.

Throughout this specification and in the claims the phrase 'methanol scrubbing unit' means a scrubbing unit configured for receiving a supply of methanol and the phrase 'acetic acid scrubbing unit' means a scrubbing unit configured for receiving a supply of acetic acid.

By 'scrubbed off-gas' is meant throughout this specification and in the claims off-gas which has been contacted with a scrubbing solvent, methanol or acetic acid as the context requires, in a scrubbing unit to produce an off-gas having a reduced methyl iodide content.

By 'used methanol' is meant throughout this specification and in the claims, methanol which has been used to scrub off-gas so as to form a stream which comprises methanol containing absorbed methyl iodide.

By 'used acetic acid' is meant throughout this specification and in the claims, acetic acid which has been used to scrub off-gas so as to form a stream which comprises acetic acid containing absorbed methyl iodide.

The present invention also provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises:

(i) supplying off-gas and acetic acid to the acetic acid scrubbing unit and withdrawing off-gas therefrom;

(ii) supplying withdrawn off-gas and methanol to the methanol scrubbing unit and contacting the off-gas and methanol therein to produce scrubbed off-gas; and (iii) withdrawing from the methanol scrubbing unit scrubbed off-gas, wherein acetic acid is supplied to the acetic acid scrubbing unit at a tick-over flow rate and said acetic acid is all or part of an acetic acid stream from a heavy ends column, preferably all or part of an acetic acid stream removed as an overhead from the heavy ends column.

The present invention also provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises:

(i) supplying off-gas and acetic acid to the acetic acid scrubbing unit and withdrawing off-gas therefrom;

(ii) supplying withdrawn off-gas and methanol to the methanol scrubbing unit and contacting the off-gas and methanol therein to produce scrubbed off-gas; and (iii) withdrawing from the methanol scrubbing unit scrubbed off gas,
wherein acetic acid is supplied to the acetic acid scrubbing unit at a tick-over flow rate and each of the acetic acid and methanol is cooled prior to supply to a scrubbing unit.

The present invention further provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises (i) supplying off-gas and acetic acid to the acetic acid scrubbing unit and withdrawing the off-gas therefrom;

(ii) supplying withdrawn off-gas and methanol to the methanol scrubbing unit and contacting the off-gas and methanol therein to produce scrubbed off-gas; and (iii) withdrawing from the methanol scrubbing unit scrubbed off-gas;
wherein acetic acid is supplied to the acetic acid scrubbing unit at a tick-over flow rate and at least a portion of the off-gas withdrawn from the methanol scrubbing unit is passed to a combustion system used for providing heat to one or more process operations of the production unit.

By 'combustion system used for providing heat to one or more process operations' is meant throughout this specification and in the claims, that the combustion system can provide heat directly to a process operation or indirectly to a process operation by means of a heat transfer medium, such as by providing heat to a process operation via steam.

Some or all embodiments of the present invention further provide for one or both of the steps:

(iv) withdrawing from the methanol scrubbing unit a used methanol stream and introducing the stream or a portion thereof, to the reactor;

(v) withdrawing from the acetic acid scrubbing unit a stream consisting essentially of acetic acid and introducing the stream, or a portion thereof, to a light ends column.

Thus, the present invention yet further provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises:

(i) supplying off-gas and acetic acid to the acetic acid scrubbing unit and withdrawing the off-gas therefrom;

(ii) supplying withdrawn off-gas and methanol to the methanol scrubbing unit and contacting the off-gas and methanol therein to produce scrubbed off-gas;

(iii) withdrawing scrubbed off-gas from the methanol scrubbing unit and passing at least a portion thereof to a combustion system used for providing heat to one or more process operations of the production unit;

(iv) optionally withdrawing from the methanol scrubbing unit a used methanol stream and introducing the stream or a portion thereof, to the reactor; and (v) optionally withdrawing from the acetic acid scrubbing unit a stream consisting essentially of acetic acid and introducing the stream, or a portion thereof, to a light ends column, wherein the acetic acid is supplied to the acetic acid scrubbing unit at a tick-over flow rate.

The present invention yet further provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises:

(i) supplying off-gas and acetic acid to the acetic acid scrubbing unit and withdrawing the off-gas therefrom;

(ii) supplying withdrawn off-gas and methanol to the methanol scrubbing unit and contacting the off-gas and methanol therein to produce scrubbed off-gas; and (iii) withdrawing from the methanol scrubbing unit scrubbed off-gas;

wherein the acetic acid is supplied to the acetic acid scrubbing unit at a tick-over flow rate and there is introduced into the methanol scrubbing unit an additional supply of methanol, the additional methanol supply being introduced into a lower portion of the scrubbing unit.

The present invention yet further provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises (i) supplying off-gas and acetic acid to the acetic acid scrubbing unit and withdrawing the off-gas therefrom;

(ii) supplying withdrawn off-gas and methanol to the methanol scrubbing unit, said methanol being supplied to an upper portion of the scrubbing unit, and contacting the off-gas and methanol therein to produce scrubbed off-gas and a used methanol stream and introducing into a lower portion of the methanol-scrubbing unit an additional supply of methanol;

(iii) withdrawing from the methanol scrubbing unit scrubbed off-gas;

(iv) withdrawing from the methanol scrubbing unit a stream comprising used methanol and fresh methanol and introducing the stream, or a portion thereof, to the reactor, wherein the acetic acid is supplied to the acetic acid scrubbing unit at a tick-over flow rate and methanol supplied to the upper and lower portions of the methanol scrubbing unit is fresh methanol.

The present invention yet further provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises (i) supplying off-gas and acetic acid to the acetic acid scrubbing unit and withdrawing the off-gas therefrom;

(ii) supplying withdrawn off-gas and methanol to the methanol scrubbing unit contacting off-gas and methanol therein, said methanol being supplied to an upper portion of the scrubbing unit, to produce scrubbed off-gas and a used methanol stream and introducing into a lower portion of the methanol scrubbing unit an additional supply of methanol;

(iii) withdrawing from the methanol scrubbing unit scrubbed off-gas; and (iv) withdrawing from the methanol scrubbing unit the used methanol and additional methanol as a combined stream and introducing the combined stream or a portion thereof to the reactor, preferably using at least one high pressure pump, more preferably using a single set of high pressure pumps, wherein acetic acid is supplied to the acetic acid scrubbing unit at a tick-over flow rate and methanol supplied to the upper and lower portions of the methanol scrubbing unit is fresh methanol.

The present invention also provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises (i) supplying off-gas and acetic acid to the acetic acid scrubbing unit and withdrawing the off-gas therefrom;

(ii) supplying withdrawn off-gas and methanol to the methanol scrubbing unit and contacting the off-gas and methanol therein to produce scrubbed off-gas;

(iii) withdrawing from the methanol scrubbing unit scrubbed off-gas and optionally passing at least a portion thereof to a combustion system used for providing heat to one or more process operations of the production unit;

(iv) optionally withdrawing from the methanol scrubbing unit a used methanol stream and introducing the stream or a portion thereof, to the reactor;

(v) optionally withdrawing from the acetic acid scrubbing unit a stream consisting essentially of acetic acid and introducing the stream, or a portion thereof, to a light ends column; and (vi) optionally introducing an additional supply of methanol into the methanol scrubbing unit, wherein acetic acid is supplied to the acetic acid scrubbing unit at a tick-over flow rate.

Typically, under non-steady state operating conditions, the availability of methanol to a scrubbing unit becomes limited or even non-existent. The tick-over flow-rate of acetic acid employed under normal operating conditions is insufficient to perform scrubbing of off-gas. Thus, the present invention also provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises:

(i) supplying off-gas and acetic acid at a tick-over flow rate to the acetic acid scrubbing unit and withdrawing off-gas therefrom;

(ii) supplying withdrawn off-gas and methanol to the methanol scrubbing unit, contacting the off-gas and methanol therein to produce scrubbed off-gas;

(iii') reducing or ceasing the supply of methanol to the methanol scrubbing unit; and (iv') increasing the flow rate of acetic acid supplied to the acetic acid scrubbing unit, contacting off-gas therein with acetic acid and withdrawing therefrom scrubbed off-gas and a used acetic, acid stream.

Preferably, in step (iii') the supply of methanol to the methanol scrubbing unit is ceased.

Steps (iii') and (iv') may be performed sequentially or simultaneously, such that the increase of the flow rate supplied to the acetic acid scrubbing unit may occur: prior to the reducing or ceasing the supply of methanol to the methanol scrubbing unit; after the reducing or ceasing the supply of methanol to the methanol scrubbing unit; or, simultaneously with the reducing or ceasing the supply of methanol to the methanol scrubbing unit. Preferably, steps (iii') and (iv') are performed such that the increase of the flow rate supplied to the acetic acid scrubbing unit occurs either prior to the reducing or ceasing the supply of methanol to the methanol scrubbing unit or simultaneously with the reducing or ceasing the supply of methanol to the methanol scrubbing unit.

The present invention also provides a method of operating an off-gas scrubbing system in an acetic acid production unit which generates off-gas comprising methyl iodide, said production unit comprising a reactor, a light ends recovery section comprising a light ends column, are acetic acid scrubbing unit and a methanol scrubbing unit which method comprises:

(i) supplying off-gas and acetic acid at a tick-over flow rate to the acetic acid scrubbing unit and withdrawing off-gas therefrom;

(ii) supplying withdrawn off-gas and methanol to the methanol scrubbing unit, contacting the off-gas and methanol therein to produce scrubbed off-gas;

(iii') reducing or ceasing the supply of methanol to the methanol scrubbing unit; and (iv') increasing the flow rate of acetic acid supplied to the acetic acid scrubbing unit, contacting off-gas therein with acetic acid and withdrawing therefrom scrubbed off-gas and a used acetic acid stream, wherein in step (i) acetic acid is obtained from one or more acetic acid streams from a heavy ends column and in step (iv')) the increased flow rate of acetic acid is provided by the addition of one or more streams of fresh acetic acid.

Preferably, the used acetic acid stream withdrawn from the acetic acid scrubbing unit, or a portion thereof, is introduced into the light ends column.

Steps (iii') and (iv') may be performed sequentially or simultaneously, such that the increase of the flowrate supplied to the acetic acid scrubbing unit may occur: prior to the reducing or ceasing the supply of methanol to the methanol scrubbing unit; after the reducing or ceasing the supply of methanol to the methanol scrubbing unit; or, simultaneously with the reducing or ceasing the supply of methanol to the methanol scrubbing unit. Preferably, steps (iii') and (iv') are performed such that the increase of the flow rate supplied to the acetic acid scrubbing unit occurs either prior to the reducing or ceasing the supply of methanol to the methanol scrubbing unit or simultaneously with the reducing or ceasing the supply of methanol to the methanol scrubbing unit.

The present invention further provides a method of operating an off-gas scrubbing system in an acetic acid production unit which generates off-gas comprising methyl iodide, said production unit comprising a reactor, a light ends recovery section comprising a light ends column and an acetic acid scrubbing unit and a methanol scrubbing unit which method comprises:

(i) supplying off-gas and acetic acid at a tick-over flow rate to the acetic acid scrubbing unit and withdrawing off-gas therefrom;

(ii) supplying withdrawn off-gas and methanol to the methanol scrubbing unit, contacting the off-gas and methanol therein to produce scrubbed off-gas;

(iii') ceasing the supply of methanol to the methanol scrubbing unit;

(iv') increasing the flow rate of acetic acid supplied to the acetic acid scrubbing unit, contacting off-gas therein with acetic acid and withdrawing therefrom scrubbed off-gas and a used acetic acid stream and optionally ceasing the supply of off-gas from the acetic acid scrubbing unit to the methanol scrubbing unit;

(v') heating off-gas withdrawn in step (iv') to a temperature above that at which acetic acid will freeze.

Preferably, the supply of scrubbed off-gas withdrawn from the acetic acid scrubbing unit (step (iv')) to the methanol scrubbing unit is ceased.

Preferably, scrubbed off-gas withdrawn from the acetic acid scrubbing unit (step (iv')), or a portion thereof, is passed directly for disposal, for example by combustion, such as by combustion in a flare system.

Steps (iii') and (iv') may be performed sequentially or simultaneously, such that the increase of the flow rate supplied to the acetic acid scrubbing unit may occur: prior to the reducing or ceasing the supply of methanol to the methanol scrubbing unit; after the reducing or ceasing the supply of methanol to the methanol scrubbing unit; or, simultaneously with the reducing or ceasing the supply of methanol to the methanol scrubbing unit. Preferably, steps (iii') and (iv') are performed such that the increase of the flow rate supplied to the acetic acid scrubbing unit occurs either prior to the reducing or ceasing the supply of methanol to the methanol scrubbing unit or simultaneously with the reducing or ceasing the supply of methanol to the methanol scrubbing unit.

The present invention also provides an apparatus for scrubbing off-gas generated in an acetic acid production unit which production unit comprises a reactor for the production of acetic acid and a light ends recovery section comprising a light ends column wherein the apparatus comprises at least:

an acetic acid scrubbing unit and a methanol scrubbing units coupled in series;

the acetic acid scrubbing unit having a first inlet for receiving a supply of acetic acid, a second inlet for receiving off-gas, a first outlet for discharging off-gas and a second outlet for discharging a stream comprising acetic acid;

the methanol scrubbing unit having a first inlet for receiving a supply of methanol, a second inlet for receiving off-gas connected to the first outlet of the acetic acid scrubbing unit, a first outlet for discharging scrubbed off-gas and a second outlet for discharging a used methanol stream and said methanol scrubbing unit is operable to scrub received off-gas with methanol to remove methyl iodide therefrom;

and wherein the acetic acid scrubbing unit is configurable for operation at a tick-over flow rate of acetic acid.

In some or all embodiments, the apparatus further comprises at least:

a heat exchange unit configured to reduce the temperature of off-gas comprising entrained methanol discharged from the methanol scrubbing unit and separating entrained methanol therefrom, said heat exchange unit connected to be in communication with the methanol scrubbing unit and adapted to receive off-gas discharged therefrom;

a heater for heating off-gas comprising entrained acetic acid discharged from the acetic acid scrubbing unit, said heater connected to be in communication with the first outlet of the acetic acid scrubbing unit and adapted to receive off-gas discharged from the acetic acid scrubbing unit; and a heater for heating off-gas comprising entrained methanol discharged from the methanol scrubbing unit, and optionally off-gas comprising entrained acetic acid discharged from the acetic acid scrubbing unit, said heater connected to be in communication with the first outlet of the methanol scrubbing unit and optionally in communication with the first outlet of the acetic acid scrubbing unit.

a combustion system used for providing heat to one or more process operations from off-gas discharged from the methanol scrubbing unit, said combustion system being coupled to the first outlet of the methanol scrubbing unit and adapted to receive off-gas discharged therefrom, for example a boiler system used for generating steam from off-gas discharged from the methanol scrubbing unit;

a flare system for combusting off-gas discharged from the acetic acid scrubbing unit, said flare system being coupled to the acetic acid scrubbing unit and adapted to receive off-gas discharged therefrom;

a flare system for combusting off-gas discharged from the methanol scrubbing unit, said flare system being coupled to the methanol scrubbing unit and adapted to receive off-gas discharged therefrom; wherein said flare system for combusting off-gas discharged from the methanol scrubbing unit may be the same flare system as the flare system for combusting off-gas discharged from the acetic acid scrubbing unit.

In some or all embodiments of the present invention yet further comprises at least:

a high pressure pump system for introducing a combined stream of used methanol and additional methanol discharged from the methanol scrubbing unit into the reactor, said high pressure pump system connected to be in communication with the first outlet of the methanol scrubbing unit, adapted to receive a stream comprising methanol withdrawn from the methanol scrubbing unit and is coupled to a feed system for the supply of methanol to the reactor and wherein said high pressure pump system comprises at least one high pressure pump, typically a set of high pressure pumps.

FIG. 1 is a schematic representation of apparatus for off-gas scrubbing in accordance with an embodiment of the invention.

Advantageously, in the present invention, under normal operating conditions, the methanol scrubbing unit is operated such that it shall perform 100% of the scrubbing duty whilst also maintaining a flow of acetic acid at a tick-over flow rate to the acetic acid scrubbing unit and thus, should non-steady state conditions arise in the production plant, the scrubbing duty can be readily switched to acetic acid by increasing the flow-rate of acetic acid to the acetic acid scrubbing unit to a flow-rate which is effective to scrub the off-gas supplied to the acetic acid scrubbing unit such that the off-gas withdrawn from the acetic acid scrubbing unit does not require further scrubbing with methanol.

Furthermore, by supplying acetic acid at a tick-over flow rate to the acetic acid scrubbing unit, ancillary equipment associated with the acetic acid scrubbing unit, such as valves and pumps, will be correctly lined out should non-steady conditions occur. Consequently, in the event of a trip (plant upset) or at plant shutdown, the methanol scrubbing unit can promptly be taken off-line and scrubbing of off-gas continued using acetic acid (in the acetic acid scrubbing unit) without incurring the types of delays which may be experienced in switching systems, for example delays due to re-alignment of valves or delays caused by low pressure to high pressure pump changeovers. Thus, if non-steady state conditions arise, the present invention provides a simplified and more efficient means of switching between scrubbing solvents.

As discussed above, typically, to improve scrubbing efficiency methanol is cooled prior to its use in a scrubbing unit and generally to temperatures below which acetic acid freezes. As a consequence the methanol scrubbing unit and associated process lines are also typically at a sufficiently low temperature to cause freezing of acetic acid. Advantageously, in the present invention, under non-steady state conditions, scrubbed off-gas withdrawn from the acetic acid scrubbing unit may by-pass the methanol scrubbing unit thereby avoiding freezing of acetic acid within the methanol scrubbing unit. Moreover, scrubbed off-gas withdrawn from the acetic acid scrubbing unit may be heated to prevent freezing of the acetic acid in process lines which are used under normal operating conditions for scrubbed off-gas withdrawn from the methanol scrubbing unit.

Furthermore, in the present invention, acetic acid and methanol solvents are supplied to different scrubbing units thus mitigating mixing of the two solvents on changeover from methanol to acetic acid or vice-versa. This provides a distinct advantage over the use of single scrubbing unit systems in which multiple solvents are used and wherein there will inherently be periods of time, such as on changeovers of solvents, when mixtures of the different solvents will be supplied to the scrubbing unit.

For efficiency purposes it may be desirable to transfer used scrubbing solvent to a catalyst storage tank. Typically the nature of the materials present in such storage tanks makes the tanks generally undesirable as repositories of methanol. In the present invention used acetic acid scrubbing solvent is unlikely to become contaminated with methanol and hence it may conveniently be transferred to catalyst storage tanks.

In addition, the present invention does not necessitate the need for additional equipment to regenerate acetic acid from used acetic acid streams. Acetic acid may be conveniently and simply regenerated by transfer to a light ends column.

As discussed above, it has been suggested in the art that used methanol streams may be transferred to methanol storage/surge tanks. Disadvantages associated with failure to effectively scrub off-gas due to undesirable high levels of methyl iodide in the methanol solvent streams may be mitigated in the present invention by supplying fresh methanol from one or more methanol storage tanks to the reactor via the methanol scrubbing unit.

Furthermore, disadvantages associated with the use of two or more sets of high pressure pumps to supply methanol to the reactor may be avoided by the present invention. Advantageously, in the present invention, a single high-pressure pump or single set of high pressure pumps may be utilised, such pump or pumps connected so as to be in communication with as outlet for discharging used methanol streams from the methanol scrubbing unit.

The present invention relates to a method of operating an off-gas scrubbing system in an acetic acid production unit. In particular, the present invention relates to a method of operating an off-gas scrubbing system in a production unit for the manufacture of acetic acid by the carbonylation of methanol with carbon monoxide in the presence of a Group VIII metal catalyst, for example at least one of rhodium and iridium.

By the term "an acetic acid production unit" it is meant a unit that produces at least acetic acid and encompasses units that co-produce acetic acid and acetic anhydride.

The present invention provides a method of operating an off-gas scrubbing system in an acetic acid production unit which generates off-gas comprising methyl iodide, said production unit-comprising a reactor, a light ends recovery section comprising a light ends column, an acetic acid, scrubbing unit and a methanol scrubbing unit which method comprises:

(i) supplying off-gas and acetic acid to the acetic acid scrubbing unit and withdrawing off-gas therefrom;

(ii) supplying withdrawn off-gas and methanol to the methanol scrubbing unit and contacting the off-gas and methanol therein to produce scrubbed off-gas; and (iii) withdrawing from the methanol scrubbing unit scrubbed off-gas, wherein acetic acid is supplied to the acetic acid scrubbing unit at a tick-over flow rate.

In the present invention, the acetic acid production unit comprises a reactor, a light ends recovery section comprising a light ends column, an acetic acid scrubbing unit and a methanol scrubbing unit. Typically, a flash zone is employed between the reactor and the light ends recovery section. Other reactors or distillation sections may also be present. Production unit equipment for the manufacture of acetic acid, for example by the carbonylation of methanol and/or a reactive derivative thereof with carbon monoxide in the presence of a Group VIII metal catalyst, and the operation thereof is well known in the art.

Off-gas streams produced in the manufacture of acetic acid, for example in the manufacture of acetic acid by the carbonylation of methanol and/or a reactive derivative thereof with carbon monoxide in the presence of a Group VIII metal catalyst, such as rhodium and/or iridium catalysts, may be produced in or from any part of the production unit, such as from one or more of the reactor(s) in a flash zone and from the light ends recovery section. Off-gas streams produced in or from any part of the acetic acid production unit may be scrubbed in accordance with the present invention.

Off-gas generated from the reactor is commonly referred to as high-pressure off-gas. Off-gas generated in a flash zone generally passes into the light ends recovery section and is removed therefrom. The light ends recovery section comprises a light ends column, a condenser section comprising one or more condensers and a phase separation vessel (decanter). Off-gas produced from the light ends recovery section may be off-gas withdrawn from the condenser section and/or withdrawn from the decanter.

Off-gas produced from the light ends recovery section is commonly referred to as low pressure off-gas.

Streams of high pressure and low pressure off-gas may be combined to generate a low-pressure off-gas.

In some or all embodiments of the present invention, off-gas to be scrubbed, is a low-pressure off-gas.

Methyl iodide is present in the off-gas, typically as entrained and/or evaporated methyl iodide.

Off-gas to be scrubbed in accordance with the present invention can vary widely in its content of methyl iodide, for example methyl iodide may be present in the off-gas in an amount of from about 1 mol % to about 20 mol %.

In addition to methyl iodide, the off-gas may comprise one or more non-condensable components, for example carbon, monoxide, inert gases, such as nitrogen and reaction by-product gases such as hydrogen, carbon dioxide and methane. The off-gas may also contain at least one of acetic acid, methyl acetate and water.

The light ends recovery section serves the dual purpose of crude acetic acid purification and of recycling methyl iodide and methyl acetate to the reactor.

Throughout this specification, including in the claims, the term 'light ends column' means a distillation column which separates crude acetic acid product (obtained from a carbonylation reactor or flash zone) from the light ends, methyl iodide and methyl acetate. Thus, the light ends column for use in the present invention will include those distillation columns referred to in the art as 'light ends distillation columns' and 'combined light ends and drying columns'. A combined light ends and drying column is a light ends column in which water is removed from the afore-mentioned crude acetic acid product so as to produce a dry acetic add product.

Typically, the feed stream to the light ends column is a vapour stream comprising acetic acid, water, carbon monoxide, methyl acetate and methyl iodide.

Typically, the vapour stream will be that obtained from a flash zone. The purpose of the flash zone is to separate the liquid reaction composition from the reactor into (i) a vapour fraction comprising water, acetic acid product, methyl acetate and methyl iodide which is then introduced into a light ends column, and (ii) a liquid traction comprising the catalyst. The liquid fraction can be recycled to the reactor.

In the light ends column, the higher boiling acetic acid is separated from the lower boiling components such as methyl iodide and methyl acetate.

The conditions and configuration under which the light ends column is operated are not critical to the present invention provided that the separation of acetic acid from methyl iodide and methyl acetate is achieved. Suitably, the light ends column may have up to 40 theoretical separation stages. The column may be operated at any suitable pressure, for example a heads pressure of from 1.0 to 3.0 barg, typically from 1.0 to 2.5 barg, and a base pressure of from 1.2 to 3.8 barg, typically from 1.2 to 3.5 barg. The operating temperature of the light ends column will depend upon a number of factors, including the composition of the feed, herds and base streams and the operating pressure. Typical base temperatures may be in the range 125° C. to 180° C. and typical heads temperatures may be in the range 105° C. to 140° C.

In general, at least two streams are removed from the light ends column, a stream comprising acetic acid product and as an overhead from the column, a vapour fraction comprising methyl iodide, methyl acetate, water, acetic acid and carbon monoxide.

The acetic acid product stream may be removed from any suitable point of the light ends column, for example, from below the feed point, or as a liquid or vapour from the base of the column.

The acetic acid product stream removed from the light ends column may, if required, be dried, for example in a drying column. A separate drying column is generally not required if the light ends column is a combined light ends distillation and drying column.

The separated water can be recycled to the reactor and/or removed from the process.

Dried acetic acid may then be passed to a heavy ends column in which propionic acid by-product is separated from dry acetic acid. The dry acid may be withdrawn from the heavy ends column as a side-draw. Additional streams comprising acetic acid may be removed from the heavy ends column, such as acetic acid streams removed as an overhead from the column.

The second part of the light ends recovery section consists of a condenser section comprising one or more condensers and/or coolers to condense the overhead vapour fraction from the light ends column to produce a liquid fraction. Any suitable method known to condense the overhead vapour fraction to the liquid phase can be employed but typically this is achieved by cooling, using, for example at least one heat exchanger. The heat exchanger(s) may be supplied with water as cooling mediums.

Those components of the overhead vapour fraction from the light ends column which are not condensed, for example carbon monoxide, carbon dioxide, inert gases, reaction by-product gases are removed from the condenser section as an off-gas stream. This off-gas stream comprises methyl iodide, present as entrained methyl iodide and/or evaporated methyl iodide, and generally also comprises some methyl acetate and water.

The liquid fraction from the condenser section comprises mainly methyl acetate, methyl iodide, water and acetic acid but it may also contain entrained or dissolved gaseous components such as carbon monoxide, carbon dioxide and inert gases.

From the condenser section, the liquid fraction may be passed to a decanter where it is separated into two layers, a lower (organic) layer comprising methyl iodide and methyl acetate and an upper (aqueous) layer comprising water.

Off-gas may also be withdrawn from the decanter.

Acetic acid is supplied to the acetic acid scrubbing unit. It will be understood by the skilled person that acetic acid suitable for use in a scrubbing unit consists essentially of acetic acid, by which is meant that it consists of at least 90% acetic acid. Thus, acetic acid supplied to the acetic acid scrubbing unit is typically dry (1 wt % or less of water) and is essentially free of methyl iodide (typically less than 100 ppm).

Suitably, acetic acid supplied to the acetic acid scrubbing unit is obtained from one or more of fresh (product) acetic acid, acetic acid streams from a light ends column, for example from a combined light ends and drying column, and acetic acid streams from a heavy ends column. Typically, fresh acetic acid is obtained from one or more storage tanks used to store fresh acetic acid.

In some or all embodiments of the present invention, acetic acid supplied to the acetic acid scrubbing unit at a tick-over flow rate is all or part of an acetic acid stream from a heavy ends column, for example all or part of an acetic acid stream removed as an overhead from a heavy ends column. Suitably, all of the acetic acid supplied to the acetic acid scrubbing unit at a tick-over flow rate is provided by all or part of an acetic acid stream removed as an overhead from a heavy ends column.

Alternatively and/or additionally, acetic acid supplied to the acetic acid scrubbing unit may be all or part of an acetic acid stream removed as a sidedraw stream from a heavy ends column.

Acetic acid supplied to the acetic acid scrubbing unit may comprise all or part of acetic acid streams removed from a heavy ends column as overhead streams, as sidedraw streams or mixtures thereof.

Under normal operating conditions, methanol is supplied to the methanol scrubbing unit and is used to scrub the off-gas to remove methyl iodide therefrom. It will be understood by the skilled person that methanol suitable for use in the methanol scrubbing unit consists essentially of methanol, by which is meant that it consists of at least 90% methanol. Thus, suitably methanol supplied to the methanol scrubbing unit may be fresh methanol. Typically, fresh methanol is obtained from one or more storage tanks used to store fresh methanol.

In general, scrubbing efficiency is improved at lower temperatures. Thus, in some or all embodiments of the present invention there is provided the further step of cooling one or both of acetic acid and methanol prior to being supplied to a scrubbing unit. Preferably, each of acetic acid and methanol is cooled prior to use in a scrubbing unit. Suitably, cooling of the acetic acid and methanol may be carried out using one or more heat exchangers.

Suitably, acetic acid for supply to a scrubbing unit is cooled to a temperature of from about 18° C. to about 50° C.

Suitably, methanol for supply to a scrubbing unit is cooled to a temperature of from about 5° C. to about 20° C.

In the present invention, under steady-state conditions, acetic acid is continuously supplied to the acetic acid scrubbing unit at a tick-over flow rate. As described above, the tick-over flow rate of acetic acid is a flow rate of acetic acid which is ineffective to achieve the required removal of methyl iodide from off-gas flowing through the acetic acid scrubbing unit such that the off-gas withdrawn from the scrubbing unit retains all or substantially all of its methyl iodide content. Consequently, in the present invention, under steady-state conditions, the methanol scrubbing unit is configured and operated such that it would provide 100% of the scrubbing duty based on the composition of the off-gas entering the acetic acid scrubbing unit.

Suitably, the tick-over flow rate of acetic acid is such that the off-gas withdrawn from the acetic acid scrubbing unit under steady state conditions retains the majority of the methyl iodide content; for example, the off-gas withdrawn from the acetic acid scrubbing unit will typically retain greater than half of its original methyl iodide content; such as at least 60%, or at least 70%, or at least 80%, or at least 90% of its original methyl iodide content. In one particular embodiment, the off-gas withdrawn from the acetic acid scrubbing unit may retain at least about 99%, such as at least about 99.9% of its methyl iodide content.

Suitably, the tick-over flow rate of acetic acid may be such that the methyl iodide content of off-gas is reduced in the acetic acid scrubbing unit to an amount that is less than half of its original methyl iodide content, such as less than 40%, or less than 30%, or less than 20%, or less than 10% of its original methyl iodide content. In one particular embodiment, the tick-over flow rate of acetic acid may be such that the methyl iodide content of off-gas is reduced in the acetic acid scrubbing unit by about 1% or less, such as by about 0.1% or less.

Suitably, the tick-over flow rate of acetic acid may be from about 1% to about 25%, for example from about 3% to about 18%, of a flow rate of acetic acid which would be sufficient to provide 100% of the scrubbing duty.

Suitably, the ratio of the tick-over flow rate of acetic acid to the flow rate of methanol is in the range 1:3 to 20, for example in the range 1:4 to 10.

Tick-over flow rates of acetic acid may differ from one acetic acid production unit to another and are influenced by the specific design of the acetic acid scrubbing unit and the production capacity of the plant. The tick-over flow rate of acetic acid is a flow rate which keeps the liquid distributers within the scrubbing unit filled with acetic acid and maintains a minimum flow over the packing and/or trays inside the scrubbing unit. Suitably, the tick-over flow rate of acetic acid may be that flow rate which achieves minimum wetting of the packing or trays within the acetic acid scrubbing unit. The flow rate of a material, such as acetic acid, required to achieve minimum wetting of packing or trays within a scrubbing unit may be readily determined by a skilled person, for example from Glitsch's rule, which is described, for example in 'Distillation Design by Henry Z Kister, 1992, pages 511-515, McGraw-Hill'.

Suitably, for acetic acid production units of capacity 600 kte/pa to 1000 kte/pa, the tick-over flow rate of acetic acid may be from about 1 te/hr to about 10 te/hr, for example from about 3 te/hr to about 7 te/hr.

Under steady-state conditions, acetic acid supplied to the acetic acid scrubbing unit is withdrawn from the scrubbing unit as a steam consisting essentially of acetic acid. The location at which the acetic acid is withdrawn from the scrubbing unit can be varied. The acetic acid stream, or at least a portion thereof, may be withdrawn from the scrubbing unit at or below the final vapour/liquid contacting stage of the scrubbing unit or alternatively as a sidedraw stream from the scrubbing unit.

Suitably, the acetic acid stream withdrawn from the acetic acid scrubbing unit, or a portion thereof, is introduced into the light ends column. Preferably, all of the acetic acid stream withdrawn from the acetic acid scrubbing unit is introduced into the light ends column. Thus, some or all embodiments of the present invention provide for a further step of withdrawing a stream from the acetic acid scrubbing unit consisting essentially of acetic acid and introducing the stream, or a portion thereof, into the light ends column. Preferably, the light ends column is a combined light ends and drying column.

The acetic acid stream withdrawn from the acetic acid scrubbing unit may be introduced at any stage of the light ends column but is preferably introduced into the lower portion of the column, for example at or below the flash zone feed point to the column.

Under steady-state operation, off-gas withdrawn from the acetic acid scrubbing unit retains or is to be considered to retain substantially all of its original methyl iodide content and therefore it is subjected to a scrubbing step. Withdrawn off-gas from the acetic acid scrubbing unit is supplied to the methanol scrubbing unit where it is contacted with methanol to reduce its methyl iodide content. Methanol supplied to the methanol scrubbing unit to scrub the off-gas flows downwardly through the packing or trays within the scrubbing unit to contact upwardly flowing off-gas and remove methyl iodide therefrom. As would be understood by a skilled person in the art, to effect scrubbing, methanol is supplied to the upper portion of the scrubbing unit, most preferably supplied at a point above the top tray or above the top of the packing of the scrubbing unit. A used methanol stream comprising methanol with absorbed methyl iodide is withdrawn from the scrubbing unit. Thus, some or all embodiments of the present invention further comprise the step of withdrawing from the methanol scrubbing unit a used methanol stream and introducing the used methanol stream, or a portion thereof, into the reactor. Suitably, the used methanol stream is withdrawn from at or near the base of the methanol scrubbing unit.

Throughout this specification and in the claims, references to the introduction of the used methanol stream and/or streams comprising the used methanol stream, and portions of such streams, to the reactor, include the introduction of said streams directly or indirectly to any reactor or section of the acetic acid production unit wherein the carbonylation of methanol occurs.

Contacting of off-gas with methanol in the methanol scrubbing unit allows the efficient removal of methyl iodide from off-gas and methyl iodide can be essentially completely removed from the off-gas, for example to about 100 ppm by volume or less, such as to about 35 ppm by volume or less.

Scrubbed off-gas is withdrawn from the methanol scrubbing unit, typically as an overhead. The scrubbed off-gas may be disposed of, for example by burning. However, in some or all embodiments of the present invention, scrubbed off-gas from the methanol scrubbing unit, or a portion thereof, may be passed directly or indirectly, suitably directly, to a combustion system used for providing heat to one or more process operations of the production unit; for example to generate steam.

As discussed above, for scrubbing purposes it is generally desirable to supply methanol to an upper portion of a scrubbing unit. However, in some or all embodiments of the present invention there is introduced into the methanol scrubbing unit an additional supply of methanol. This additional methanol is not intended to be used for scrubbing. Thus, preferably the additional methanol supply is introduced into a lower portion of the methanol scrubbing unit. Suitably, additional methanol introduced into a lower portion of the methanol scrubbing unit, may be introduced at or near to the base of the scrubbing unit, preferably at a point below the inlet of the off-gas.

Suitably, a methanol supply, for example a fresh methanol supply, may be divided, with a first portion of the methanol supplied to the upper portion of the methanol unit and a second portion of the methanol introduced into the lower portion of the scrubbing unit.

Desirably, methanol supplied to one or both, preferably both, of the upper and lower portions of the methanol scrubbing unit is fresh methanol. The fresh methanol may be obtained from one or more storage tanks used to store fresh methanol.

The additional methanol and used methanol streams may be withdrawn from the methanol scrubbing unit as a combined stream. The combined stream or a portion thereof may be introduced into the reactor, preferably using at least one high pressure pump, typically a single set of high pressure pumps.

In some or all embodiments of the present invention fresh methanol is supplied to each of the upper and lower portions of the methanol scrubbing unit, a combined stream of used methanol and fresh methanol is withdrawn from the scrubbing unit and the combined stream, or a portion thereof, is introduced into the reactor, using at least one high pressure pump, preferably a single set of high pressure pumps.

Alternatively and/or additionally, a supply of fresh methanol, for example from one or more methanol storage tanks, is split with a first portion of the methanol supplied to the methanol scrubbing unit to scrub the off-gas and a second portion of the methanol combined with a used methanol stream withdrawn from the methanol scrubbing unit. Thus, in some or all embodiments of the present invention, methanol supplied to the methanol scrubbing unit in step (ii) is a first portion of a fresh methanol supply and a second portion of the fresh methanol supply is combined with a used methanol stream withdrawn from the methanol scrubbing unit and the combined stream, or a portion thereof, is introduced to the reactor. Desirably, the fresh methanol supply is obtained from one or more storage tanks used to store fresh methanol. Furthermore, the combined stream, or a portion thereof, may be introduced into the reactor using a single high pressure pump or a single set of high pressure pumps, for pumping all, or a portion of the combined stream, to the reactor.

Typically, under non-steady state operating conditions the availability of methanol for scrubbing is limited or even non-existent. Despite the lack of availability of methanol, the present invention allows scrubbing of off-gas to be effectively continued by increasing the flow rate of acetic acid to the acetic acid scrubbing unit from a tick-over flow rate to a flow rate which is effective to perform 100% of the scrubbing duty. Thus, in one or more embodiments of the present invention, there is provided the further steps:
(iii') reducing or ceasing the supply of methanol to the methanol scrubbing unit;
(iv') increasing the flow rate of acetic acid supplied to the acetic acid scrubbing unit, contacting off-gas therein with acetic acid and withdrawing therefrom scrubbed off-gas and a used acetic acid stream.

Thus, the present invention also provides a method of operating an off-gas scrubbing system in an acetic acid production unit which generates off-gas comprising methyl iodide, said production unit comprising a reactor, a light ends recovery section comprising a light ends column, an acetic acid scrubbing unit and a methanol scrubbing unit which method comprises:
(i) supplying off-gas and acetic acid at a tick-over flow rate to the acetic acid scrubbing unit and withdrawing off-gas therefrom;
(ii) supplying withdrawn off-gas and methanol to the methanol scrubbing unit, contacting the off-gas and methanol therein to produce scrubbed off-gas;
(iii') reducing or ceasing the supply of methanol to the methanol scrubbing unit;
(iv') increasing the flow rate of acetic acid supplied to the acetic acid scrubbing unit, contacting off-gas therein with acetic acid and withdrawing therefrom scrubbed off-gas and a used acetic acid stream.

Preferably, in step (iii') the supply of methanol to the methanol scrubbing unit is ceased.

In step (iv') the flow rate of acetic acid is increased from a tick-over flow rate to a rate which is effective to scrub the off-gas such that its methyl iodide content is reduced and reduced to an extent that a further scrubbing using methanol is not required. Preferably, the flow rate of acetic acid to the acetic acid scrubbing unit is increased such that off-gas withdrawn from the scrubbing unit comprises methyl iodide in an amount of about 100 ppm by volume or less, for example in an amount of about 35 ppm by volume or less.

Suitably, in step (iv'), for acetic acid production plants of 600 to 1000 kte/pa capacity, the increased flow rate of acetic acid may be from about 10 te/hr to about 45 te/hr, for example from about 15 te/hr to about 37 te/hr.

Additional acetic acid required to provide an increased flow rate of acetic acid may be obtained from one or more sources. Suitable sources of acetic acid include fresh acetic acid, one or more acetic acid streams from a light ends column, one or more acetic acid streams from a heavy ends column and mixtures thereof. In some or all embodiments of the present invention, the acetic acid for use in step (iv') is a mixture of fresh acetic acid and one or more acetic acid streams from a heavy ends column. Preferably, acetic acid supplied to the acetic acid scrubbing unit in step (iv') is an acetic acid stream removed from a heavy ends column as an overhead stream, a sidedraw stream, or mixtures thereof, together with fresh acetic acid.

In some or all embodiments of the present invention, in step (i) acetic acid is obtained from one or more acetic acid streams from a heavy ends column and in step (iv') the increased flow rate of acetic acid is provided by the addition of one or more streams of fresh acetic acid.

Suitably, in step (iv') the used acetic acid stream is withdrawn from the scrubbing unit at or below the final vapour/liquid contacting stage in the scrubbing unit. However, alternatively or additionally, a used acetic acid stream may be withdrawn from the scrubbing unit, for example as a sidedraw stream.

In some or all embodiments of the present invention, a used acetic acid stream or a portion thereof, withdrawn from the acetic acid scrubbing unit is introduced into at least one of the light ends column and one or more storage tanks used to store acetic acid.

A used acetic acid stream withdrawn in step (iv') may be introduced into the light ends column at any stage of the column but preferably is introduced into the lower portion of the column, for example at or below the reactor or flash zone feed point to the column. In the light ends column, the used acetic acid stream is separated into acetic acid and methyl iodide components and the separated acetic acid may be removed from the light ends column, for example, from a point below the introduction of the feed from the flash zone, or where a flash zone is not used, below the introduction of the feed from the reactor. Acetic acid removed from the light ends column may be further purified in one or more distillation stages. Methyl iodide may be removed from the light ends column as an overhead and ultimately returned to the reactor.

Suitably, in step (iii') the methanol supply to the methanol scrubbing unit is ceased. Where additional methanol is supplied to the lower portion of the methanol scrubbing unit, this supply may be continued. Suitably, however, it is reduced or ceased, preferably ceased.

Steps (iii') and (iv') may be carried out sequentially, such that step (iii') is carried out prior to step (iv') or step (iv') is carried out prior to step (iii'). Alternatively, steps (iii') and (iv') may be carried out simultaneously.

Preferably, during steady state operation, scrubbed off-gas withdrawn from the methanol scrubbing unit is passed to a combustion system used for providing heat to one or more process operations of the production unit. However, under non-steady state conditions, wherein off-gas is scrubbed with acetic acid and not with methanol, it is preferred in this instance to dispose of the scrubbed off-gas. Thus, suitably, off-gas withdrawn from the acetic acid scrubbing unit may be disposed of, for example by combustion, such as combustion in a flare system.

Thus, scrubbed off-gas withdrawn from the acetic acid scrubbing unit may be supplied to the methanol scrubbing unit withdrawn therefrom and passed, or a portion thereof, for disposal, for example by combustion, such as by combustion in a flare system. Desirably, however, scrubbed off-gas withdrawn from the acetic acid scrubbing unit in step (iv') by-passes the methanol scrubbing unit and is instead passed directly for disposal from the acetic acid scrubbing unit. Thus, in some or all embodiments of the present invention the supply of off-gas withdrawn from the acetic acid scrubbing unit (step (iv')) to the methanol scrubbing unit is ceased and off-gas withdrawn from the acetic acid scrubbing unit, or a portion thereof, may be, and preferably is, passed directly for disposal, for example by combustion, such as by combustion in a flare system.

In general, scrubbed off-gas may contain small amounts of entrained scrubbing solvent, by which is meant scrubbing solvent which is carried overhead from the scrubbing unit by the off-gas flowing through the scrubbing unit, typically said scrubbing solvent being carried overhead as a vapour formed within the scrubbing unit although some scrubbing solvent may be carried within the off-gas in the form of droplets. Removal of the entrained solvent may be effected by cooling of the off-gas taken from the overhead section of the scrubbing unit. Suitably, cooling may be applied to the off-gas such that the off-gas may be cooled to temperatures at or below which the scrubbing solvent condenses out from the off-gas. In the present invention, under steady state conditions, methanol is used as the scrubbing solvent and the gas in the vent lines and/or overhead lines from the methanol scrubbing unit may be cooled to temperatures below about 17° C.

Suitably, in the present invention, under non-steady state conditions, off-gas scrubbed with acetic acid is sent for disposal through these vent lines. To prevent freezing of acetic acid within the vent lines, it is preferable that, prior to disposal, scrubbed off-gas withdrawn from the acetic acid scrubbing unit comprising entrained acetic acid is heated to a temperature above that at which the acetic acid will freeze. Thus, in some or all embodiments of the present invention there is provided the further step:

(v') heating off-gas withdrawn in step (iv') to a temperature above which acetic acid will freeze.

Suitably, off-gas withdrawn from the acetic acid scrubbing unit is heated to a temperature above which acetic acid will freeze, in one or more heat exchangers, and subsequently may be disposed of, for example by combustion.

Desirably, off-gas withdrawn at or close to atmospheric pressure from the acetic acid scrubbing unit is heated to temperatures above about 16.7° C.; operation at super-atmospheric pressures or even sub-atmospheric pressures are possible, preferably in the range of from 0 to 5 barg, and the temperature to which the off-gas withdrawn from the acetic acid scrubbing unit is heated should be adjusted accordingly to prevent freezing of the acetic acid.

Once steady-state conditions are resumed and methanol becomes available for scrubbing, off-gas scrubbing can be switched from acetic acid back to methanol by reducing the flow-rate of acetic acid to the acetic acid scrubbing unit to a tick-over flow rate, supplying methanol to the methanol scrubbing unit, withdrawing off-gas from the acetic acid scrubbing unit and contacting the withdrawn off-gas with methanol in the methanol scrubbing unit to produce a scrubbed off-gas. The sequence by which the switch back from acetic acid scrubbing to methanol scrubbing should be such that no off-gas which has not been subjected to either acetic acid scrubbing or methanol scrubbing is disposed of; preferably, methanol is supplied to the methanol scrubbing unit and the off-gas withdrawn from the acetic acid scrubbing unit should be passed to the methanol scrubbing unit before the flow rate of acetic acid being supplied to the acetic acid scrubbing unit is reduced to a tick-over flow rate.

Suitably, off-gas to be scrubbed in accordance with the present invention is off-gas comprising methyl iodide which is generated in an acetic acid production unit which operates a process for the carbonylation of methanol with carbon monoxide in the presence of a Group VIII metal carbonylation catalyst and methyl iodide to produce acetic acid. Processes and Group VIII metal catalysts for the carbonylation of methanol are well-known.

The carbonylation process may be conducted as a homogeneous process or as a heterogeneous process.

Suitably, in a heterogeneous carbonylation process the Group VIII metal carbonylation catalyst, such as rhodium and/or iridium is supported on an inert support, such as carbon and activated carbon. Optionally, the catalyst may also comprise at least one metal promoter. Suitable metal promoters include ruthenium, iron, nickel, lithium and cobalt. The methanol reactant may be fed to the process in the liquid and/or vapour phase. Methyl iodide and optional water are preferably fed to the process in the liquid phase.

Suitably, a homogeneous liquid phase carbonylation process employs a liquid reaction composition comprising a Group VIII metal carbonylation catalyst, methyl iodide, methyl acetate and water.

Suitably, the Group VIII metal carbonylation catalyst in the liquid reaction composition is an iridium and/or rhodium-containing compound which is soluble in the liquid reaction composition. The iridium and/or rhodium-carbonylation catalyst may be added to the liquid reaction composition in any suitable form which dissolves in the liquid reaction composition or is convertible to a soluble form.

Examples of suitable iridium-containing compounds which may be used in the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-$, $[Ir(CO)_2Br_2]^-$, $[Ir(CO)_2I_2]^-$, $[Ir(CH_3)I_3(CO)_2]^-$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-free complexes of iridium such as acetates, oxalates and acetoacetates.

Suitably, the concentration of iridium catalyst in the liquid reaction composition is in the range 100 to 6000 ppm by weight of iridium.

Examples of suitable rhodium-containing compounds which may be used in the liquid reaction composition include $[Rh(CO)_2Cl]_2$, $[Rh(CO)_2I]_2$, $[Rh(Cod)Cl]_2$, rhodium (III) chloride, rhodium (III) chloride trihydrate, rhodium (III) bromide, rhodium (III) iodide, rhodium (III) acetate, rhodium dicarbonylacetylacetonate, $RhCl_3(PPh_3)_3$ and $RhCl(CO)(PPh_3)_2$.

Suitably, the concentration of rhodium catalyst in the liquid reaction composition is in the range from 1 ppm up to its limit of solubility in the reactor and/or product recovery system, typically in the range 10 to 1500 ppm by weight of rhodium.

Where the Group VIII metal carbonylation catalyst is an iridium carbonylation catalyst, the liquid reaction composition may optionally contain a promoter selected from the group consisting of ruthenium, osmium and rhenium Where the Group VIII metal carbonylation catalyst is a rhodium carbonylation catalyst, the liquid reaction composition may optionally contain a promoter selected from alkali metals and/or an organic iodide, such as a quaternary ammonium iodide. Preferably the promoter is lithium iodide.

The concentration of methyl acetate in the liquid reaction composition for rhodium-catalysed carbonylation is suitably in the range 0.1 to 70% by weight and for iridium-catalysed carbonylation is suitably in the range 1 to 70% by weight.

Water is present in the liquid reaction composition. Water is formed in situ in the liquid reaction composition by the esterification reaction between methanol and acetic acid product. Additional water may be introduced to the carbonylation reactor together with or separately from other components of the liquid reaction composition. Preferably, the concentration of water in the liquid reaction composition is in the range 0.1 to 15% by weight, more preferably 1 to 15% by weight.

The concentration of methyl iodide used in the liquid reaction composition is preferably in the range 1 to 20% by weight.

A solvent, preferably acetic, may be used in the liquid reaction composition.

The carbonylation process employs carbon monoxide. The carbon monoxide may be essentially pure or may contain impurities such as carbon dioxide, methane, nitrogen, hydrogen and noble gases.

Suitably, the partial pressure of carbon monoxide is from about 1 to about 70 bar, for example from about 1 to about 35 bar.

Suitably, the carbonylation process is carried out at a total pressure from about 10 to about 100 barg.

Suitably, the carbonylation process is carried out at a temperature from about 100 to about 300° C.

The carbonylation process may be operated as either a batch or continuous, preferably as a continuous process.

The present invention also provides an apparatus for scrubbing off-gas generated in an acetic acid production unit which production unit comprises a reactor for the production of acetic acid and a light ends recovery section comprising a light ends column wherein the apparatus comprises at least:
- an acetic acid scrubbing unit and a methanol scrubbing units coupled in series;
- the acetic acid scrubbing unit having a first inlet for receiving a supply of acetic acid, a second inlet for receiving off-gas, a first outlet for discharging off-gas and a second outlet for discharging a stream comprising acetic acid;
- the methanol scrubbing unit having a first inlet for receiving a supply of methanol, a
- second inlet for receiving off-gas connected to the first outlet of the acetic acid scrubbing unit, a first outlet for discharging off-gas and a second outlet for discharging a used methanol stream and said methanol scrubbing unit is operable to scrub received off-gas with methanol to remove methyl iodide therefrom;

and wherein the acetic acid scrubbing unit is configurable for operation at a tick-over flow rate of acetic acid.

For the acetic acid scrubbing unit to be configurable for operation at a tick-over flow rate, the scrubbing column will be configured such that the acetic acid scrubbing solvent will be spread evenly across the trays and/or packing of the scrubbing column such that it is wetted at the tick-over flow rate.

In some or all embodiments of the present invention, the methanol scrubbing unit has an additional inlet for receiving a supply of methanol such that the first inlet is located in an upper portion of the methanol scrubbing unit and the additional inlet is located in a lower portion, such as at or near to the base, of the methanol scrubbing unit.

The equipment for and the operation of scrubbing units to remove methyl iodide from off-gas with scrubbing solvents, such as methanol and acetic acid, are known in the art, for example as described in CN 1289172C, U.S. Pat. No. 4,241,219 and CN 100358610C.

Each of the acetic acid and methanol scrubbing units may be any suitable scrubbing unit known in the art which is capable of operating to remove methyl iodide from off-gas, which is generated in an acetic acid production unit, using a scrubbing solvent such as methanol or acetic acid.

Suitably, each of the acetic acid and methanol scrubbing units may conveniently be in the form of a column containing trays or packing such as metal helices, Raschig rings and the like. Suitably, a column contains at least 5 theoretical separation stages and in general contains 5 to 30 theoretical separation stages.

Suitably, each of the acetic acid and methanol scrubbing units may be operated at a pressure of from about 0.1 barg to about 30 barg, typically from about 0.1 barg to 10 barg.

The acetic acid and methanol scrubbing units may each be a stand-alone unit or they may be combined into an integrated unit.

Suitably, the acetic acid scrubbing unit further comprises a first heat exchanger for cooling acetic acid to be supplied to the acetic acid scrubbing unit, said heat exchanger being coupled to the acetic acid scrubbing unit and a source of acetic acid. Desirably, the first heat exchanger is coupled to a source of acetic acid which source is selected from one or more storage tanks used to store fresh acetic acid and all or part of an acetic acid-containing stream withdrawn as an overhead from a heavy ends column.

Desirably, the methanol scrubbing unit comprises a second heat exchanger for cooling methanol for supply to the methanol scrubbing unit, said heat exchanger being coupled to the methanol scrubbing unit and a source of methanol.

Suitably, the first and second heat exchangers may be any suitable heat exchange system known in the art capable of cooling the acetic acid and methanol solvents to the desired temperatures for use in the acetic acid and methanol scrubbing units respectively.

The present invention further provides an apparatus for scrubbing off-gas generated in an acetic acid production unit which production unit comprises a reactor for the production of acetic acid and a light ends recovery section comprising a light ends column wherein the apparatus comprises at least:
- an acetic acid scrubbing unit and a methanol scrubbing units coupled in series;
- the acetic acid scrubbing unit having a first inlet for receiving a supply of acetic acid, a second inlet for receiving off-gas, a first outlet for discharging off-gas and a second outlet for discharging a stream comprising acetic acid;
- the methanol scrubbing unit having a first inlet and an additional inlet for receiving a supply of methanol, said first inlet being located in an upper portion of the scrubbing unit and the additional inlet being located in a lower portion of the scrubbing unit, a second inlet for receiving off-gas and connected to the first outlet of the acetic acid scrubbing unit, a first outlet, for discharging off-gas and a second outlet for discharging a used methanol stream and said methanol scrubbing unit is operable to scrub received off-gas with methanol to remove methyl iodide therefrom;
- a first heat exchanger for cooling the supply of acetic acid to the acetic acid scrubbing unit, said heat exchanger being coupled to the acetic acid scrubbing unit and a source of acetic acid;
- a second heat exchanger for cooling the supply of methanol to the methanol scrubbing unit, said heat exchanger being coupled to the methanol scrubbing unit and a source of methanol;
- and wherein the acetic acid scrubbing unit is configurable for operation at a tick-over flow rate of acetic acid.

In some or all embodiments, the apparatus further comprises a combustion system used for providing heat to one or more process operations; for example a boiler system for generating steam from off-gas discharged from the methanol scrubbing unit, said boiler system being coupled to the first outlet of the methanol scrubbing unit and adapted to receive off-gas discharged therefrom.

The apparatus may also comprise a flare system for combusting off-gas discharged from the acetic acid scrubbing unit, said flare system being coupled to the acetic acid scrubbing unit and adapted to receive off-gas discharged therefrom. Flare systems for the combustion of scrubbed off-gas are well known in the art and any suitable flare system may be employed in the present invention.

Scrubbed off-gas discharged from the methanol scrubbing unit may comprise entrained methanol scrubbing solvent. To remove such entrained methanol, the off-gas may be cooled or condensed, for example by cooling to a temperature of from −30° C. to 0° C., in a third heat exchanger. Suitably, the third heat exchanger may be any heat exchange system known in the art which is capable of cooling off-gas such that entrained methanol is separated therefrom, such as a refrigerant-condenser or other similar apparatus. Thus, preferably, the apparatus further comprises a third heat exchanger for cooling off-gas comprising entrained methanol discharged from the methanol scrubbing unit to a temperature such that the entrained methanol is separated therefrom as a liquid, said heat exchanger being coupled to the methanol scrubbing unit and adapted to receive off-gas discharged therefrom.

Under non-steady state conditions, off-gas is scrubbed with acetic acid in the acetic acid scrubbing unit and a scrubbed off-gas having a reduced methyl iodide content discharged therefrom. The scrubbed off-gas may contain entrained acetic acid scrubbing solvent. To prevent condensing and/or and freezing of acetic acid within vent lines used, under steady state conditions, for scrubbed off-gas discharged from the methanol scrubbing unit the apparatus may further comprise a heater to heat scrubbed off-gas discharged from the acetic acid scrubbing unit.

The heater may be any suitable heater which is capable of heating off-gas comprising entrained acetic acid to a temperature above the freezing point of acetic acid, preferably in the range of from 16.7° C. to 50° C. Suitable heaters include, for example heat exchangers. Suitable heat exchangers are well known in the art, such as shell heat- and tube type heat exchangers.

Thus, in some or all embodiments of the present invention, the apparatus further comprises at least:
  a heat exchange unit configured to reduce the temperature of off-gas comprising entrained methanol discharged from the methanol scrubbing unit and separating entrained methanol therefrom coupled to the methanol scrubbing unit and adapted to receive off-gas discharged therefrom;
  a heater for heating off-gas comprising entrained acetic acid discharged from the acetic acid scrubbing unit, said heater connected to be in communication with the first outlet of the acetic acid scrubbing unit and adapted to receive off-gas discharged from the acetic acid scrubbing unit,
  a combustion system used for providing heat to one or more process operations from off-gas discharged from the methanol scrubbing unit, said combustion system being coupled to the first outlet of the methanol scrubbing unit and adapted to receive off-gas discharged therefrom, for example a boiler system used for generating steam from off-gas discharged from the methanol scrubbing unit;
  a flare system for combusting off-gas discharged from the acetic acid scrubbing unit, said flare system being coupled to the acetic acid scrubbing unit and adapted to receive off-gas discharged therefrom; and
  a flare system for combusting off-gas discharged from the methanol scrubbing unit, said flare system being coupled to the methanol scrubbing unit and adapted to receive off-gas discharged therefrom; wherein said flare system for combusting off-gas discharged from the methanol scrubbing unit may be the same flare system as the flare system for combusting off-gas discharged from the acetic acid scrubbing unit.

In some or all embodiments, the apparatus is configured such that the second outlet of the acetic acid scrubbing unit is connected to be in communication with a feed system for the light ends column such that the acetic acid stream discharged from the acetic acid scrubbing unit may be introduced into the light ends column.

In some or all embodiments of the present invention, the apparatus further comprises a high pressure pump system for introducing into the reactor methanol streams withdrawn from the second outlet of the methanol scrubbing unit. The methanol stream withdrawn from the methanol scrubbing unit may consist essentially of used methanol (that is methanol comprising absorbed methyl iodide) but preferably is a combined methanol stream comprising fresh and used methanol. Alternatively and/or additionally, additional methanol may be combined with the used methanol stream or the combined stream comprising fresh and used methanol withdrawn from the methanol scrubbing unit outside of the methanol scrubbing unit. The high pressure pump system comprises at least one high pressure pump, preferably the high pressure pump system comprises one set of high pressure pumps.

In some or all embodiments, the apparatus further comprises at least:
  a heat exchanger for cooling off-gas comprising entrained methanol discharged from the methanol scrubbing unit and separating entrained methanol therefrom coupled to the methanol scrubbing unit and adapted to receive off-gas discharged therefrom;
  a combustion system used for providing heat to one or more process operations from off-gas discharged from the methanol scrubbing unit, said combustion system being coupled to the first outlet of the methanol scrubbing unit and adapted to receive off-gas discharged therefrom, for example a boiler system used for generating steam from off-gas discharged from the methanol scrubbing unit;
  a flare system for combusting off-gas discharged from the acetic acid scrubbing unit, said flare system being coupled to the acetic acid scrubbing unit and adapted to receive off-gas discharged therefrom;
  a flare system for combusting off-gas discharged from the methanol scrubbing unit, said flare system being coupled to the methanol scrubbing unit and adapted to receive off-gas discharged therefrom; wherein said flare system for combusting off-gas discharged from the methanol scrubbing unit may be the same flare system as the flare system for combusting off-gas discharged from the acetic acid scrubbing unit; and
  a high pressure pump system for introducing a combined stream of used methanol and additional methanol discharged from the methanol scrubbing unit into the reactor, said high pressure pump system connected to be in communication with the second outlet of the methanol scrubbing unit, adapted to receive a stream comprising methanol withdrawn from the methanol scrubbing unit and is coupled to a feed system for the supply of methanol to the reactor.

Embodiments of the invention will now be illustrated by way of example only and with reference to FIG. 1. In FIG. 1, the apparatus comprises an acetic acid scrubbing unit (2), a methanol scrubbing unit (3) and heat exchangers (4) and (5). For ease of discussion, transfer lines, such as pipes and process streams flowing therein are referred to using the term 'stream'.

In use, an off-gas stream (1), suitably a low pressure off-gas stream, containing an amount of methyl iodide and optionally one or more additional components, such as the non-condensable components carbon monoxide, carbon dioxide and inert gases, is supplied to the acetic acid scrubbing unit (2) through an inlet (20). A stream of liquid acetic acid (6), such as an acetic acid stream withdrawn from a heavy ends column as an overhead, a sidedraw, or a mixture thereof, is passed through a heat exchanger (4) to cool the acetic acid, for example to a temperature of from about 18° C. to about 50° C. and is introduced into the acetic acid scrubbing unit (2) through inlet (7) at a tick-over flow rate. A liquid acetic acid stream (19) is discharged from the acetic acid scrubbing unit (2) through outlet (18) at or near to the base of the acetic acid scrubbing unit (2) and suitably is introduced into a light ends column of an acetic acid production unit (not shown), for example into a combined light ends and drying column. An off-gas stream with no reduction or substantially no reduction in the amount of methyl iodide is discharged, suitably as an overhead stream, from the acetic acid scrubbing unit (2) through outlet (8) as stream (9) and is supplied to the methanol scrubbing unit (3) through inlet (10). A stream of liquid methanol (11), suitably fresh methanol, is passed through a heat exchanger (5) to cool the methanol, for example to a temperature of from about 5° C. to about 20° C. prior to being supplied through inlet (12) to the methanol scrubbing unit (3). Optionally, additional methanol (13), preferably fresh methanol, may be introduced to the methanol scrubbing unit (3) through an additional inlet (16), and preferably is introduced into the lower portion of the methanol scrubbing unit (3). The off-gas stream (9) discharged from the acetic acid scrubbing unit (2) is passed upwardly through the methanol scrubbing unit (3) where it is brought into counter-current contact with the stream of liquid methanol (11) to remove methyl iodide from the off-gas stream (9). A liquid stream (14) comprising used methanol is withdrawn from the methanol scrubbing unit (3) through outlet (15), suitably at or near to the base of the methanol scrubbing unit (3) and preferably is passed to a reactor for the carbonylation of methanol to produce acetic acid (not shown). Where an additional methanol supply (13) is supplied to the methanol scrubbing unit (3), it may be combined therein with used methanol and the combined stream withdrawn from the methanol scrubbing unit (3) through outlet (15), suitably at or near to the base of the methanol scrubbing unit (3) as stream (14) and preferably is passed to a reactor for the carbonylation of methanol to produce acetic acid (not shown). Preferably, stream (14) is passed to a reactor using a single set of high pressure pumps (not shown). A scrubbed off-gas stream (21) is discharged from the methanol scrubbing unit (3), suitably as an overhead from the methanol scrubbing unit (3) through outlet (17) and may be disposed of, but preferably is passed to a combustion system used for providing heat to one or more process operations, such as a boiler (not shown) for the generation of steam.

Under non-steady state conditions, the stream of liquid methanol (11) supplied to the methanol scrubbing unit (3) is reduced or ceased, preferably ceased. The flow rate of the cooled liquid acetic acid stream (6) supplied to the acetic acid scrubbing unit (2) through inlet (7) is increased to a rate which is effective to scrub the off-gas stream (1) supplied to the acetic acid scrubbing unit (2) through inlet (20) and remove methyl iodide therefrom. A scrubbed off-gas stream (9) is discharged through outlet (8) from the acetic acid scrubbing unit (2) and disposed of, for example by combustion in a flare. Optionally, prior to disposal the off-gas stream (9) may be heated in a heater (not shown) to vaporise entrained acetic acid and/or ensure that any entrained acetic acid does not freeze in any downstream units, for example heated to a temperature of from about 16.7° C. to about 50° C. A used liquid acetic acid stream (19) is withdrawn through outlet (18) from the acetic acid scrubbing unit (2) and preferably is introduced into a light ends column of an acetic acid production unit (not shown), suitably into a combined light ends and drying column.

The invention claimed is:

1. A method of operating an off-gas scrubbing system in an acetic acid production unit which acetic acid production unit generates off-gas comprising methyl iodide, said production unit comprising a reactor, a light ends recovery section comprising a light ends column, an acetic acid scrubbing unit and a methanol scrubbing unit which method comprises:
   (i) supplying off-gas and acetic acid to the acetic acid scrubbing unit and withdrawing off-gas therefrom;
   (ii) supplying withdrawn off-gas and methanol to the methanol scrubbing unit and contacting the off-gas and methanol therein to produce scrubbed off-gas; and
   (iii) withdrawing from the methanol scrubbing unit scrubbed off-gas;
   wherein the acetic acid is supplied to the acetic acid scrubbing unit at a tick-over flow rate.

2. The method according to claim 1, further comprising passing the scrubbed off-gas withdrawn from the methanol scrubbing unit or at least a portion thereof directly or indirectly to a combustion system, the combustion system being used for providing heat to one or more process operations of the production unit.

3. The method according to claim 1, further comprising receiving an acetic acid stream removed as an overhead from a heavy ends column, wherein all or part of the acetic acid stream provides the acetic acid to the acetic acid scrubbing unit.

4. The method according to claim 1, further comprising introducing into a lower portion of the methanol scrubbing unit an additional supply of methanol.

5. The method according to claim 4, wherein the additional methanol is fresh methanol.

6. The method according to claim 4, further comprising withdrawing from the methanol scrubbing unit as a combined stream the additional supply of methanol and a used methanol stream formed by contacting of off-gas and methanol in step (ii); and introducing the combined stream or a portion thereof is introduced into the reactor.

7. The method according to claim 6, wherein the combined stream is introduced into the reactor using a single set of high pressure pumps.

8. The method according to claim 4, wherein further comprising combining outside the methanol scrubbing unit the additional supply of methanol and a used methanol stream formed by contacting of off-gas and methanol in step (ii) to form a combined stream; and introducing the combined stream or a portion thereof is introduced into the reactor.

9. The method according to claim 8, wherein the combined stream is introduced into the reactor using a single set of high pressure pumps.

10. The method according to claim 1, which method comprises the further steps:
   (iii') reducing or ceasing the supply of methanol to the methanol scrubbing unit;
   (iv') increasing a flow rate of acetic acid supplied to the acetic acid scrubbing unit, contacting off-gas therein with acetic acid and withdrawing therefrom scrubbed off-gas and a used acetic acid stream.

11. The method according to claim 10, wherein the acetic acid for use in step (iv') is a mixture of fresh acetic acid and one or more acetic acid streams from a heavy ends column.

12. The method according to claim 10, further comprising introducing the used acetic acid stream or a portion thereof into at least one of the light ends column and one or more storage tanks used to store acetic acid.

13. The method according to claim 10 wherein scrubbed off-gas withdrawn in step (iv') comprises entrained acetic acid, the method further comprising heating the scrubbed off-gas to a temperature above that at which the acetic acid will freeze.

14. The method according to claim 10, wherein the-acetic acid scrubbing unit and methanol scrubbing units are coupled in series;

the acetic acid scrubbing unit has a first inlet for receiving a supply of acetic acid, a second inlet for receiving off-gas, a first outlet for discharging off-gas and a second outlet for discharging a stream comprising acetic acid;

the methanol scrubbing unit has a first inlet and an additional inlet for receiving a supply of methanol, said first inlet being located in an upper portion of the scrubbing unit and the additional inlet being located in a lower portion of the scrubbing unit, a second inlet for receiving off-gas and connected to the first outlet of the acetic acid scrubbing unit, a first outlet for discharging off-gas and a second outlet for discharging a used methanol stream and said methanol scrubbing unit scrubs received off-gas with methanol to remove methyl iodide therefrom; and the acetic acid scrubbing unit operates at the tick-over flow rate of acetic acid.

15. The method according to claim 14, wherein:

a first heat exchanger is coupled to the acetic acid scrubbing unit and a source of acetic acid, said first heat exchanger cooling the supply of acetic acid to the acetic acid scrubbing unit;

a second heat exchanger is coupled to the methanol scrubbing unit and a source of methanol, said second heat exchanger cooling the supply of methanol to the methanol scrubbing unit; and a third heat exchanger is coupled to the methanol scrubbing unit and receives off-gas discharged therefrom, said third heat exchanger cooling off-gas comprising entrained methanol discharged from the methanol scrubbing unit and separating the entrained methanol as a liquid therefrom.

16. The method according to claim 14, wherein:

a heater connected to be in communication with the first outlet of the acetic acid scrubbing unit and receives and heats off-gas discharged from the acetic acid scrubbing unit, said off-gas comprising entrained acetic acid from the acetic acid scrubbing unit.

17. The method according to claim 14, further comprising:

introducing, via a high pressure pump system, a combined stream of used methanol and additional methanol discharged from the methanol scrubbing unit into the reactor, said high pressure pump system being connected to be in communication with the second outlet of the methanol scrubbing unit and to conduct a stream comprising methanol withdrawn from the methanol scrubbing unit to a feed system for the supply of methanol to the reactor and wherein said high pressure pump system comprises at least one high pressure pump.

* * * * *